(12) United States Patent
Hite et al.

(10) Patent No.: US 12,023,344 B2
(45) Date of Patent: Jul. 2, 2024

(54) TOPICAL OTIC, OPHTHALMIC, AND NASAL CORTICOSTEROID FORMULATIONS

(71) Applicant: Axar Laboratories, Inc., Corona, CA (US)

(72) Inventors: William Hite, Winchester, CA (US); Nilesh Parikh, Irvine, CA (US); Kapil Swain, Corona, CA (US); Jonathan Moreno, Corona, CA (US)

(73) Assignee: FamyGen Life Sciences, Inc., Framingham, MA (US)

( * ) Notice: Subject to any disclaimer, the term of this patent is extended or adjusted under 35 U.S.C. 154(b) by 0 days.

(21) Appl. No.: 17/824,478

(22) Filed: May 25, 2022

(65) Prior Publication Data

US 2024/0000801 A1    Jan. 4, 2024

(51) Int. Cl.

| | | |
|---|---|---|
| *A61K 31/573* | (2006.01) | |
| *A61K 9/00* | (2006.01) | |
| *A61K 9/10* | (2006.01) | |
| *A61K 31/56* | (2006.01) | |
| *A61K 31/58* | (2006.01) | |
| *A61K 47/02* | (2006.01) | |
| *A61K 47/10* | (2017.01) | |
| *A61K 47/18* | (2017.01) | |
| *A61K 47/36* | (2006.01) | |
| *A61K 47/44* | (2017.01) | |

(52) U.S. Cl.
CPC .......... *A61K 31/573* (2013.01); *A61K 9/0014* (2013.01); *A61K 9/10* (2013.01); *A61K 31/56* (2013.01); *A61K 31/58* (2013.01); *A61K 47/02* (2013.01); *A61K 47/10* (2013.01); *A61K 47/183* (2013.01); *A61K 47/186* (2013.01); *A61K 47/36* (2013.01); *A61K 47/44* (2013.01)

(58) Field of Classification Search
CPC .............................. A61K 9/0048; A61K 31/573
See application file for complete search history.

(56) References Cited

U.S. PATENT DOCUMENTS

| | | | |
|---|---|---|---|
| 4,136,177 A * | 1/1979 | Lin ............ | A61K 9/0048 |
| | | | 514/777 |
| 5,540,930 A | 7/1996 | Guy et al. | |
| 6,359,016 B2 | 3/2002 | Singh et al. | |
| 7,001,615 B1 | 2/2006 | Singh et al. | |
| 7,795,316 B1 | 9/2010 | Kabra | |
| 8,653,055 B2 | 2/2014 | Fange et al. | |
| 2002/0107238 A1* | 8/2002 | Bandyopadhyay | A61P 31/04 |
| | | | 514/227.8 |
| 2005/0069590 A1 | 3/2005 | Buehler et al. | |
| 2009/0215735 A1 | 8/2009 | Castillo | |

FOREIGN PATENT DOCUMENTS

| | | | | |
|---|---|---|---|---|
| WO | WO-0037080 A1 * | 6/2000 | ........... | A61K 31/137 |
| WO | WO-2007106381 A2 * | 9/2007 | ........... | A61K 31/192 |
| WO | WO-2020134688 A1 * | 7/2020 | ........... | C12P 19/04 |
| WO | WO-2021156813 A2 * | 8/2021 | ........... | A61K 31/573 |

OTHER PUBLICATIONS

J. Zhang et.al. J. Am. Ceram. Soc., 89 [4] 1440-1442 (2006) (Year: 2006).*

Allergan, Pred Forte prescribing information, 2017, Allergan.

* cited by examiner

*Primary Examiner* — Theodore R. Howell
*Assistant Examiner* — Pierre P Eleniste
(74) *Attorney, Agent, or Firm* — ArentFox Schiff LLP

(57) ABSTRACT

The disclosure provides pharmaceutical topical otic, ophthalmic, or nasal aqueous suspension formulations that comprise a corticosteroid; a chelating agent; a xanthan gum; an ionic tonicity agent; a pH from 5 to 6; and balance water. Such formulations comprise amounts of each of the xanthan gum and the ionic tonicity agent that together result in the formulation having: (i) a viscosity of from 4000 centipoises ("cps") to 8000 centipoises ("cps"), and (ii) an osmolality of from 250 milliosmoles ("mOsm") to 350 mOsm, and (iii) are readily redispersible.

15 Claims, No Drawings

TOPICAL OTIC, OPHTHALMIC, AND NASAL CORTICOSTEROID FORMULATIONS

FIELD

The disclosure relates to topical otic, ophthalmic, and nasal formulations of corticosteroids having excellent physical stability and re-dispersibility properties.

BACKGROUND

Steroids are organic compounds with 17 core carbon atoms bonded in three fused cyclohexane and one fused cyclopentane ring. The two main steroid groups are corticosteroids (mineralocorticoids and glucocorticoids) and sex steroids (progestogens, androgens, and estrogens). Mineralocorticoids are produced in the adrenal cortex and play a critical role in regulating concentrations of minerals, most importantly sodium and potassium, in extracellular fluids. influence salt and water balances (electrolyte balance and fluid balance). Most steroids used in ophthalmology are glucocorticoids, which activate glucocorticosteroid receptors and have anti-inflammatory and immunosuppressive activity.

Due to their lipophilicity, glucocorticoids have the ability to passively diffuse across cell membranes into the cytoplasm, though there is some evidence for facilitated transport by transporter proteins as well. In the cytoplasm, glucocorticoids bind glucocorticoid receptors which then homodimerize (GR2), translocate into the nucleus, and bind glucocorticoid response elements (GREs) in the promoter regions of corticosteroid responsive genes. GR2 bound to GREs activate the transcription of the associated genes, which include anti-inflammatory genes such as Annexin-1, SLP-1, MKP-1, and IκB-a. GR2 can also bind negative GREs to suppress gene expression. Further, GR2 negatively interacts with CREB-binding protein (CBP), which is a transcriptional co-activator of several proinflammatory genes with nuclear factor-κB (NF-κB). The negative GR2-CBP/NF-κB interaction switches off the expression of inflammatory genes otherwise activated by CBP/NF-κB, including cytokines, chemokines, adhesion proteins, and inflammatory enzymes, receptors, and proteins.

The synthetic steroid prednisolone has both glucocorticoid and mineralocorticoid receptor activity and has the chemical structure:

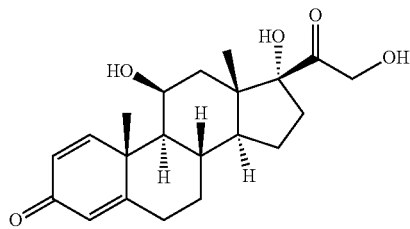

U.S. Pat. No. 5,540,930 (the "930 patent") discloses topical-ophthalmic suspensions of soft corticosteroids that contain nonionic: (a) polymer, (b) surfactant, and (c) tonicity agent. The 930 patent's aqueous suspensions of soft corticosteroids are for therapeutic use in the eye, ear, or nose. The suspensions are purportedly stable and possess the advantageous property of remaining in a redispersion-ready state, even after extended periods of storage and settling. The suspensions of the 930 patent allegedly solve a need for "aqueous suspensions of corticosteroids such as LE which can be formulated without agglomeration."

The 930 patent is based on the assertion that "[u]nexpectedly, common tonicity agents such as aqueous solutions containing 0.9% NaCl, 0.1% EDTA, or phosphate buffer, even in concentrations as low as 1 mM, cannot be employed to provide stable aqueous suspensions of corticosteroids . . . ." The 930 patent emphasizes criticality of the polymer, surfactant, and tonicity being nonionic since it has now been discovered that the presence of ions is the major cause of caking." Nonionic diols such as glycerin or mannitol "rather than the commonly used sodium chloride" are identified as the preferred tonicity agents. The 930 patent defines "[s]oft drugs" as "biologically active chemical components characterized by predictable in vivo metabolism to non-toxic derivatives after they provide their therapeutic effect." And it teaches that "[l]oteprednol etabonate ("LE") is a known soft corticosteroid based on the known inactive metabolite prednisolone acetate of the active drug prednisolone."

U.S. Pat. No. 7,795,316 (the "316 patent") teaches topical-ophthalmic, aqueous-suspensions of tobramycin and dexamethasone that contain xanthan gum and ionic species in amounts sufficient to limit interactions between tobramycin and xanthan gum so that no precipitates or clumps of tobramycin and xanthan gum are formed and such that the viscosity of the suspensions is not elevated above 700 centipoises. The 316 patent teaches that the xanthan gum used in its aqueous suspensions must be deacetylated so that the viscosity of those suspension are stable for a period of 18 months after their manufacture. The aqueous suspensions have a pH in the range of 5 to 6.

The 316 patent teaches that pharmaceutical grade xanthan gum should be utilized and explains the importance of deacetylating xanthan gum in Examples 1 and 2. Also in Example 2, the 316 patent teaches the following method for deacetylating xanthan gum. Xanthan gum was weighed and slowly added to water in a vessel while mixing. 2.5 ml of 1 N NaOH or equivalent per 1 g of xanthan gum was added and mixed for 20 minutes. 1.66 ml of 1N HCl or equivalent per 1 g of xanthan gum was then added. Purified water was added to adjust to the target weight, followed by mixing for 15 minutes. The deacetylated xanthan gum was then filtered through an appropriate filter e.g., a 1.2 µm filter.

Example 1 of the 316 patent discloses the preparation of formulations comprising tobramycin, dexamethasone, and xanthan gum that has not been deacetylated. The ingredients of those formulations and their viscosities are reported in Table 1A (reproduced below). As can be seen, the Table 1A formulations 107201 and 107209 have a high degree of qualitative and quantitative relatedness. They differ in only three ways. The former comprises more sodium chloride and has a lower pH than the latter. The former is pH adjusted with hydrochloric acid whereas the latter is pH adjusted with sulfuric acid. And the former has a lower viscosity than the latter.

TABLE 1A

| | Formulation Number | |
|---|---|---|
| | 107201 W/V % | 107209 W/V % |
| INGREDIENTS | | |
| Tobramycin | 0.3 | 0.3 |
| Dexamethasone | 0.1 | 0.1 |
| Xanthan Gum | 0.9 | 0.9 |
| Sodium chloride | 0.42 | 0.08 |
| Tyloxapol | 0.05 | 0.05 |
| Boric Acid | 0.5 | 1 |
| Disodium Edetate | 0.01 | 0.01 |
| Sodium Hydroxide | Adjust pH to 5.5 | Adjust pH to 5.7 |
| Hydrochloric Acid | Adjust pH to 5.5 | None |
| Sulfuric Acid | None | Adjust pH to 5.7 |
| Purified Water | Qs to 100% | Qs to 100% |
| RESULTS | | |
| Viscosity at shear rate 6 sec−1 (cps) | 418 | 642 |

Example 1 of the 316 patent discloses that the formulations described in its Table 1A were subjected to accelerated stability testing and reported in Table 1B (reproduced below). The 316 patent states its Table 1B shows the pH and viscosities of the Table 1A formulations, which were prepared using xanthan gum that has not been deacetylated, decrease upon storage. This eventually makes the formulations unstable. Specifically, the uniform nature of the suspensions was lost.

TABLE 1B

Stability of pH and Viscosity of Tobramycin/Dexamethasone Formulation Prepared using Non-Deacetylated Xanthan Gum

| | 107201 pH | 10729 | 107201 Viscosity of Formulation (cps) | 107209 |
|---|---|---|---|---|
| Initial | 5.48 | 5.74 | 418 | 642 |
| 40° C., 4 Weeks | 5.33 | 5.56 | 187 | 217 |
| 40° C., 8 Weeks | 5.08 | 5.36 | 86 | 141 |
| 40° C., 16 Weeks | 4.86 | 4.89 | 25 | 37 |
| 50° C., 1 Week | 5.37 | 5.73 | 175 | 240 |
| 50° C., 2 Weeks | 5.20 | 5.25 | 95 | 160 |
| 50° C., 4 Weeks | 5.10 | 5.14 | 48 | 91 |
| 50° C., 8 Weeks | 4.70 | 4.81 | Not Uniform | Not Uniform |
| 60° C., 1 Week | 5.20 | 5.16 | 68 | 132 |
| 60° C., 2 Weeks | Not Uniform | 4.83 | Not Uniform | 43 |
| 60° C., 4 Weeks | Not Uniform | Not Uniform | Not Uniform | Not Uniform |

Example 2 of the 316 patent discloses the preparation of a formulation comprising tobramycin, dexamethasone, and xanthan gum that has been deacetylated. The ingredients of that formulation, 108536, and its viscosity are reported in Table 2A (reproduced below). As can be seen, the Table 2A formulation differs qualitatively from the 107201 and 107209 formulations by containing propylene glycol, sodium sulfate, and benzalkonium chloride and by lacking boric acid and sulfuric acid (as compared to formulation 101209 only). The 108536 formulation differs quantitatively from the 107201 and 107209 formulations by having and an intermediate pH and amount of sodium chloride and a lower amount of xanthan gum. The 108536 formulation has the same amount of tobramycin, dexamethasone, tyloxapol, and disodium edetate as the 107201 and 107209 formulations.

TABLE 2A

| | Formulation Number 108536 W/V % |
|---|---|
| INGREDIENTS | |
| Tobramycin | 0.3 |
| Dexamethasone | 0.1 |
| Xanthan Gum | 0.6 |
| Sodium chloride | 0.24 |
| Propylene Glycol | 0.6 |
| Tyloxapol | 0.05 |
| Sodium Sulfate (Anhydrous) | 0.25 |
| Disodium Edetate | 0.01 |
| Benzalkonium Chloride | 0.01 |
| Sodium Hydroxide | Adjust pH to 5.75 |
| Hydrochloric Acid | Adjust pH to 5.75 |
| Purified Water | Qs to 100% |
| RESULTS | |
| Viscosity at shear rate 6 sec−1 (cps) | 116 |
| Simulated In Vivo Viscosity at shear rate 6 sec−1 (cps) | 1059 |
| Viscosity of Formulation as a % of Simulated In Vivo Viscosity | 11% |

Example 2 of the 316 patent discloses that the formulation described in its Table 2A was subjected to accelerated stability testing and reported in Table 2B (reproduced below). The 316 patent states that its Table 2B shows the pH values of the Table 2A formulation, which were prepared using xanthan gum that has been deacetylated, unlike the 107201 and 107209 formulations. The 316 patent states that, as a result, the viscosity of the 108536 formulation remained stable or increased during storage, rather than decreasing as did the 107201 and 107209 formulations.

TABLE 2B

Stability of pH and Viscosity of Tobramycin/Dexamethasone Formulations Prepared Using Deacetylated (Pre-treated) Xanthan Gun

| | Formulation Number 108536 | |
|---|---|---|
| Analysis | pH | Pre-dose Viscosity (cps) |
| Initial | 5.84 | 116 |
| 40° C., 4 Weeks | 5.80 | 166 |
| 40° C., 8 Weeks | 5.81 | 167 |
| 40° C., 12 Weeks | 5.81 | 181 |
| 40° C., 16 Weeks | ND | ND |
| 40° C., 26 Weeks | ND | ND |
| 50° C., 1 Week | 5.79 | ND |
| 50° C., 2 Weeks | 5.78 | 152 |
| 50° C., 4 Weeks | 5.76 | 179 |
| 50° C., 8 Weeks | 5.73 | 271372 |
| 50° C., 16 Weeks | ND | NA |
| 60° C., 1 Week | 5.79 | 150 |
| 60° C., 2 Weeks | 5.78 | 172 |
| 60° C., 3 Weeks | ND | ND |
| 60° C., 4 Weeks | 5.66 | 235 |

ND = Not Determined

Summary of Various Embodiments

Certain embodiments described herein provide pharmaceutical topical otic, ophthalmic, or nasal aqueous suspension formulations that comprise, or consist essentially of, between 0.001% w/v and 5% w/v of a corticosteroid, or a pharmaceutically acceptable salt thereof. In such embodiments, the corticosteroid is a cortisone, a prednisone, a prednisolone, a dexamethasone, a betamethasone, a mometasone, a triamcinolone, a fludrocortisone, a fluticasone, a deoxycorticosterone, an aldosterone, a beclometasone, a loteprednol, or a combination thereof and the pharmaceutically acceptable salt for each of such corticosteroids is an acetate, a furoate, a propionate, a fumarate, a phosphate, a sodium, a sodium phosphate, a sulfate, or a tartrate.

Certain embodiments described herein provide pharmaceutical topical otic, ophthalmic, or nasal aqueous suspension formulations that comprise, or consist essentially of, between 0.001% w/v and 5% w/v of the corticosteroid, or the pharmaceutically acceptable salt thereof as set forth in the immediately preceding paragraph; between 0.3% w/v and 1.5% w/v of a xanthan gum; between 0.001% w/v and 2% w/v an ionic tonicity agent that is a calcium chloride, a magnesium chloride, a potassium chloride, a sodium chloride, a sodium sulfate, or a combination thereof. Such formulations possess an osmolality of from 250 milliosmoles ("mOsm") to 350 mOsm; a viscosity of from 4000 centipoises ("cps") to 8000 cps; a pH from 5 to 6; and water. Such formulations are also redispersible within 60 seconds.

In some embodiments, such formulations further comprise, or consist essentially of, between 0.001% w/v and 2% w/v of a chelating agent that is an ethylenediaminetetraacetic acid ("EDTA"); an ethylene glycol tetraacetic acid, and an ethylenediamine-N,N'-disuccinic acid ("EDDS"), or a combination thereof; and/or between 0.001% w/v and 2% w/v of a nonionic surfactant that is a tyloxapol, a polysorbate 20, a polysorbate 60, a polysorbate 80, a polyethoxylated castor oil, or a combination thereof; and/or between 0.001% w/v and 2% w/v of a nonionic tonicity agent that is at propylene glycol, glycerol, mannitol, sorbitol, xylitol, erythritol, lactitol, maltitol, isomalt, or a combination thereof.

In some embodiments, the corticosteroid can be the prednisolone; the chelating agent can be the EDTA; the ionic tonicity agent can be the sodium chloride, the sodium sulfate, or a combination thereof; the nonionic surfactant can be the tyloxapol; and the nonionic tonicity agent can be the propylene glycol.

In some embodiments, the formulation comprises, or consists essentially of, between 0.25% w/v and 1.25% w/v of the prednisolone; and/or between 0.2% w/v and 0.5% w/v of the EDTA; and/or between 0.3% w/v and 1.0% w/v of the xanthan gum; and/or between 0.25% w/w and 0.75% w/v of the sodium chloride; and/or between 0.05% w/v and 0.15% w/v of the sodium sulfate; between 0.025% w/v and 0.25% w/v of the tyloxapol; and/or between 0.25% w/v and 0.75% w/v of the propylene glycol.

Certain embodiments described herein provide pharmaceutical topical otic, ophthalmic, or nasal aqueous suspension formulations that comprise, or consist essentially of, between 0.001% w/v and 5% w/v of a corticosteroid, or a pharmaceutically acceptable salt thereof. In such embodiments, the corticosteroid is a cortisone, a prednisone, a prednisolone, a dexamethasone, a betamethasone, a mometasone, a triamcinolone, a fludrocortisone, a fluticasone, a deoxycorticosterone, an aldosterone, a beclometasone, a loteprednol, or a combination thereof and the pharmaceutically acceptable salt for each of such corticosteroids is an acetate, a furoate, a propionate, a fumarate, a phosphate, a sodium, a sodium phosphate, a sulfate, or a tartrate.

Certain embodiments described herein provide pharmaceutical topical otic, ophthalmic, or nasal aqueous suspension formulations that comprise, or consist essentially of, between 0.001% w/v and 5% w/v of the corticosteroid, or the pharmaceutically acceptable salt thereof as set forth in the immediately preceding paragraph; between 0.3% w/v and 1.5% w/v of a non-deacetylated xanthan gum; between 0.001% w/v and 2% w/v an ionic tonicity agent that is a calcium chloride, a magnesium chloride, a potassium chloride, a sodium chloride, a sodium sulfate, or a combination thereof. Such formulations possess an osmolality of from 250 mOsm to 350 mOsm; a viscosity of 250 cps or more; a pH from 5 to 6; and water. Such formulations are also 70% viscosity stable for one week at 50° C.

In some embodiments, such formulations further comprise, or consist essentially of, between 0.001% w/v and 2% w/v of a chelating agent that is an EDTA; an EDDS, or a combination thereof; and/or between 0.001% w/v and 2% w/v of a nonionic surfactant that is a tyloxapol, a polysorbate 20, a polysorbate 60, a polysorbate 80, a polyethoxylated castor oil, or a combination thereof; and/or between 0.001% w/v and 2% w/v of a nonionic tonicity agent that is at propylene glycol, glycerol, mannitol, sorbitol, xylitol, erythritol, lactitol, maltitol, isomalt, or a combination thereof.

In some embodiments, the corticosteroid can be the prednisolone; the chelating agent can be the EDTA; the ionic tonicity agent can be the sodium chloride, the sodium sulfate, or a combination thereof; the nonionic surfactant can be the tyloxapol; and the nonionic tonicity agent can be the propylene glycol.

In some embodiments, the formulation comprises, or consists essentially of, between 0.25% w/v and 1.25% w/v of the prednisolone; and/or between 0.2% w/v and 0.5% w/v of the EDTA; V and/or between 0.3% w/v and 1.0% w/v of the xanthan gum; and/or between 0.25% w/w and 0.75% w/v of the sodium chloride; and/or between 0.05% w/v and 0.15% w/v of the sodium sulfate; between 0.025% w/v and 0.25% w/v of the tyloxapol; and/or between 0.25% w/v and 0.75% w/v of the propylene glycol.

Certain embodiments described herein provide methods of treating an ophthalmic disorder in a patient in need of such treatment, the methods involving the step of topically administering to ocular tissue of the patient a topical, a therapeutically effective amount of an ophthalmic corticosteroid formulation described herein. In such embodiments, the ophthalmic disorder can be a steroid-responsive inflammation of the ocular tissue.

In some embodiments, the therapeutically effective amount of the formulation is from 10 μl to 200 μl thereof. In some embodiments, the therapeutically effective amount of the formulation is about 20 μl, about 25 μl, about 30 μl, about 35 μl, about 40 μl, about 45 μl, about 50 μl, 55 μl, 60 μl, 65 μl, 70 μl, 75 μl, 80 μl, 85 μl, 90 μl, 95 μl, or 1000 μl of the formulation. In some embodiments, the ocular tissue is a cornea, a palpebral conjunctiva, a bulbar conjunctiva, and an anterior chamber, an eyelid, a sclera, a limbus, or a combination thereof. In some embodiments, the formulation is administered from once daily to eight times per day. In some embodiments, the formulation is administered one time per day, two times per day, three times per day, four times per day, five times per day, six times per day, seven times per day, and eight times per day, In some embodiments, the formulation is administered from one day to twenty-one consecutive days

DETAILED DESCRIPTION

The present inventors have investigated several scientific and technical aspects of formulating topical otic, ophthalmic, and nasal formulations of corticosteroids. One aspect investigated by the present inventors was the extent and rate of such formulations' re-dispersibility. Another aspect investigated was the storage-stability of such formulations in regards of viscosity. Non-limiting embodiments of methods of manufacturing formulations and the ingredients of the so-manufactured formulations are described in Example 1. Non-limiting embodiments of a redispersion assay and the results of the redispersion experiments carried out by the present inventors on the formulations set forth in Example 1 are described in Example 2. Non-limiting embodiments of a viscosity assay and the results of the viscosity experiments carried out by the present inventors on the formulations set forth in Example 3 are described in Example 3.

The present inventors unexpectedly found that, in direct contradiction to the teachings of the prior art, the formulations described herein unexpectedly exhibited excellent redispersion properties despite comprising high concentrations of EDTA of greater than 0.1% w/v and high concentrations of ionic polymer xanthan gum of greater than 0.3% w/v. In some embodiments, the topical, otic, ophthalmic, and nasal formulations described herein demonstrate a redispersion time in the Example 2 redispersion assay of 60 seconds or less, 50 seconds or less, 45 seconds or less, 40 seconds or less, 35 seconds or less, 30 seconds or less, 25 seconds or less, or 20 seconds or less, 15 seconds or less, 10 seconds or less, or 5 seconds or less. Such formulations are referred to as redispersible within 60 seconds, 50 seconds, 45 seconds, 40 seconds, 35 seconds, 30 seconds, 25 seconds, or 20 seconds, 15 seconds, 10 seconds, or 5 seconds.

The present inventors further unexpectedly found that, in direct contradiction to the teachings of the prior art, the formulations described herein unexpectedly exhibited excellent storage stability properties in regards of viscosity despite comprising high concentrations of non-deacetylated ionic polymer xanthan gum of greater than 0.3% w/v.

In some embodiments, the topical, otic, ophthalmic, and nasal formulations described herein comprise a corticosteroid in particulate form and are therefore suspension formulations. Corticosteroids useful in the formulations described herein include cortisol, cortisone, prednisone, prednisolone, methylprednisolone, dexamethasone, betamethasone, mometasone, triamcinolone, fludrocortisone, fluticasone, deoxycorticosterone, aldosterone, beclometasone, and loteprednol. Any of these corticosteroids may be used in the form of their pharmaceutically acceptable salts such as acetate, furoate, propionate, fumarate, phosphate, sodium, sodium phosphate, sulfate, or tartrate. In such embodiments, the formulations may comprise corticosteroid, or a pharmaceutically acceptable salt thereof, at a concentration of 0.001% w/v, 0.005% w/v, 0.01% w/v, 0.05% w/v, 0.1% w/v, 0.25% w/v, 0.5% w/v, 0.75% w/v, 1.0% w/v, 1.25% w/v, 1.5% w/v, 1.75% w/v, 2.0% w/v, 2.25% w/v, 2.5% w/v, 2.75% w/v, 3.0% w/v, 3.25% w/v, 3.5% w/v 3.75% w/v, 4.0% w/v, 4.25% w/v, 4.5% w/v, 4.75% w/v, 5.0% w/v, or ranges between any of said corticosteroid concentrations. The formulations may comprise combinations of the corticosteroids, in amounts that individually or in aggregate achieve(s) the stated corticosteroids, or pharmaceutically acceptable salts thereof, concentrations.

In some embodiments, the topical, otic, ophthalmic, and nasal formulations described herein comprise a tonicity agent. Ionic tonicity agents useful in the formulations described herein include calcium chloride, magnesium chloride, potassium chloride, sodium chloride, and sodium sulfate. Nonionic tonicity agents useful in the formulations described herein include propylene glycol, glycerol, mannitol, sorbitol, xylitol, erythritol, lactitol, maltitol, and isomalt. In such embodiments, the formulations may comprise tonicity agent at a concentration of 0.001% w/v, 0.005% w/v, 0.01% w/v, 0.05% w/v, 0.1% w/v, 0.2% w/v, 0.3% w/v, 0.4% w/v, 0.5% w/v, 0.6% w/v, 0.7% w/v, 0.8% w/v, 0.9% w/v, 1.0% w/v, 1.1% w/v, 1.2% w/v, 1.3% w/v, 1.4% w/v, 1.5% w/v, 1.6% w/v, 1.7% w/v, 1.8% w/v, 1.9% w/v, 2.0% w/v, or ranges between any of said tonicity agent concentrations. The formulations may comprise combinations of tonicity agent, in amounts that individually or in aggregate achieve(s) said tonicity agent concentrations. Further in such embodiments, the formulations may comprise an osmolality of 150 mOsm, 200 mOsm, 250 mOsm, 275 mOsm, 290 mOsm, 300 mOsm, 310 mOsm, 325 mOsm, or ranges between any of said osmolalities. The formulations may comprise combinations of tonicity agent, in amounts that individually or in aggregate achieve(s) said tonicity agent concentrations and/or said osmolalities.

In some embodiments, the topical, otic, ophthalmic, and nasal formulations described herein comprise a chelating agent such as EDTA, EGTA, or EDDS. In such embodiments, the formulations may comprise chelating agent at a concentration of 0.001% w/v, 0.005% w/v, 0.01% w/v, 0.05% w/v, 0.1% w/v, 0.2% w/v, 0.3% w/v, 0.4% w/v, 0.5% w/v, 0.6% w/v, 0.7% w/v, 0.8% w/v, 0.9% w/v, 1.0% w/v, 1.1% w/v, 1.2% w/v, 1.3% w/v, 1.4% w/v, 1.5% w/v, 1.6% w/v, 1.7% w/v, 1.8% w/v, 1.9% w/v, 2.0% w/v, or ranges between any of said chelating agent concentrations. The formulations may comprise combinations of chelating agents, in amounts that individually or in aggregate achieve(s) said chelating agent concentrations.

In some embodiments, the topical, otic, ophthalmic, and nasal formulations described herein comprise a polymer, including nonionic and/or ionic polymers. Suitable nonionic polymers include polyethylene glycol, hydroxyethyl cellulose, hydroxypropylmethyl cellulose, methyl cellulose, carboxymethyl cellulose, polyvinyl pyrrolidone, and polyvinyl alcohol. Suitable ionic polymers include polyacrylates (e.g., carbopols and carbomers), alginates, chitosans, hyaluronic acid, and xanthan gum. In such embodiments, the formulations may comprise polymers at a concentration of 0.001% w/v, 0.005% w/v, 0.01% w/v, 0.05% w/v, 0.1% w/v, 0.25% w/v, 0.5% w/v, 0.75% w/v, 1.0% w/v, 1.25% w/v, 1.5% w/v, 1.75% w/v, 2.0% w/v, 2.25% w/v, 2.5% w/v, 2.75% w/v, 3.0% w/v, 3.25% w/v, 3.5% w/v 3.75% w/v, 4.0% w/v, 4.25% w/v, 4.5% w/v, 4.75% w/v, 5.0% w/v, or ranges between any of said polymer concentrations. The formulations may comprise combinations of polymers, in amounts that individually or in aggregate achieve(s) the stated polymer concentrations. In some embodiments, the xanthan gum is not deacetylated In some embodiments, the formulations comprise multiple ionizable excipients, including ionic polymer, such as xanthan gum, in amounts that on mass balance achieve to a viscosity of 10 cps, 25 cps, 50 cps, 100 cps, 125 cps, 150 cps, 175 cps, 200 cps, 200 cps, 225 cps, 250 cps, 275 cps, 300 cps, 325 cps, 350 cps, 375 cps, 400 cps, 425 cps, 450 cps, 475 cps, 500 cps, 600 cps, 700 cps, 800 cps, 900 cps, 1000 cps, 1250 cps, 1500 cps, 1750 cps, 2000 cps, 2250 cps, 2500 cps, 2750 cps, 3000 cps, 3250 cps, 3500 cps, 3750 cps, 4000 cps, 4250 cps, 4500 cps, 4750 cps, 5000 cps, 5250 cps, 5500 cps, 5750 cps, 6000 cps, 6250 cps, 6500 cps, 6750 cps, 7000 cps, 7250 cps, 7500 cps, 7750 cps, 8000 cps, 8250 cps, 8500 cps, 8750 cps, 9000 cps, 9250 cps, 9500 cps, 9750 cps, 10,000 cps, or ranges between any of said viscosities.

In some embodiments, topical otic, ophthalmic, and nasal formulations described herein exhibit storage stability in regards of viscosity. In such embodiments, the formulation maintains a viscosity of at least 60%, at least 70%, at least 80%, at least 90%, at least 95%, at least 97%, or at least 99% of its initial viscosity after storage for one, two, three, four, eight, or sixteen weeks, at 40° C., 50° C., or 60° C. The initial viscosity of the formulation is measured within a period of not more than 24 hours post manufacture in which the temperature is maintained between 4° C. and 30° C. The initial and storage viscosities are determined with the viscosity assay described in Example 3. Such formulations are referred to as, respectively, 60%, 70%, 80%, 90%, 95%, 97%, or 99% viscosity stable for one, two, four, eight, or sixteen weeks, at 40° C., 50° C., or 60° C.

In such embodiments, the formulation, relative to its initial viscosity, demonstrates a decrease in viscosity of less than 60%, 50%, 40%, 30%, 20%, 10%, 5%, or 1% after storage for one, two, four, eight, or sixteen weeks, at 40° C., 50° C., or 60° C. Such formulations are referred to as 60%, 50%, 40%, 30%, 20%, 10%, 5%, or 1% viscosity stable within for one, two, four, eight, or sixteen weeks, at 40° C., 50° C., or 60° C.

In some embodiments, the topical, otic, ophthalmic, and nasal formulations described herein comprise a nonionic surfactant. Suitable nonionic surfactants include tyloxapol, polyoxyethylene sorbitan esters, such as polysorbate 20, polysorbate 60, and polysorbate 80; polyethoxylated castor oils, such as cremaphor, polyethoxylated hydrogenated castor oils, such as HCO-40; and poloxamers. In such embodiments, the formulations may comprise nonionic surfactant at a concentration of 0.001% w/v, 0.005% w/v, 0.01% w/v, 0.05% w/v, 0.1% w/v, 0.2% w/v, 0.3% w/v, 0.4% w/v, 0.5% w/v, 0.6% w/v, 0.7% w/v, 0.8% w/v, 0.9% w/v, 1.0% w/v, 1.1% w/v, 1.2% w/v, 1.3% w/v, 1.4% w/v, 1.5% w/v, 1.6% w/v, 1.7% w/v, 1.8% w/v, 1.9% w/v, 2.0% w/v, or ranges between any of said nonionic surfactant concentration. The formulations may comprise combinations of nonionic surfactants, in amounts that individually or in aggregate achieve(s) the stated nonionic surfactant concentrations.

In some embodiments, the topical, otic, ophthalmic, and nasal formulations described herein comprise an antibiotic. Suitable antibiotics include ampicillin, amoxicillin, azithromycin, cephalexin, ciprofloxacin, clavulanate, clindamycin, doxycycline, gatifloxacin, penicillin, tobramycin, levofloxacin, metronidazole, moxifloxacin, sulfamethoxazole, and trimethoprim. In such embodiments, the formulations may comprise antibiotic at a concentration of 0.001% w/v, 0.005% w/v, 0.01% w/v, 0.05% w/v, 0.1% w/v, 0.25% w/v, 0.5% w/v, 0.75% w/v, 1.0% w/v, 1.25% w/v, 1.5% w/v, 1.75% w/v, 2.0% w/v, 2.25% w/v, 2.5% w/v, 2.75% w/v, 3.0% w/v, 3.25% w/v, 3.5% w/v 3.75% w/v, 4.0% w/v, 4.25% w/v, 4.5% w/v, 4.75% w/v, 5.0% w/v, or ranges between any of said antibiotic concentrations. The formulations may comprise combinations of antibiotic, in amounts that individually or in aggregate achieve(s) the stated antibiotic concentrations.

In some embodiments, the topical, otic, ophthalmic, and nasal formulations described herein comprise an antiviral. Suitable antivirals include acyclovir, amantadine, ampligin, boceprevir, bolaxivir, famciclovir, imiquimod, imunovir, ganciclovir, molupirnavir, remdesivir, rimantadine, saquinavir, trifluridine, and vidarabine. In such embodiments, the formulations may comprise antiviral at a concentration of 0.001% w/v, 0.005% w/v, 0.01% w/v, 0.05% w/v, 0.1% w/v, 0.25% w/v, 0.5% w/v, 0.75% w/v, 1.0% w/v, 1.25% w/v, 1.5% w/v, 1.75% w/v, 2.0% w/v, 2.25% w/v, 2.5% w/v, 2.75% w/v, 3.0% w/v, 3.25% w/v, 3.5% w/v 3.75% w/v, 4.0% w/v, 4.25% w/v, 4.5% w/v, 4.75% w/v, 5.0% w/v, or ranges between any of said antiviral concentrations. The formulations may comprise combinations of antivirals, in amounts that individually or in aggregate achieve(s) the stated antiviral concentrations.

In some embodiments, the topical, otic, ophthalmic, and nasal formulations described herein comprise a topical anesthetic. Suitable topical anesthetics include benzocaine, butamben, cocaine, dibucaine, lidocaine, oxybuprocaine, pramoxine, proxymetacaine (proparacaine), and tetracaine. In such embodiments, the formulations may comprise topical anesthetic at a concentration of 0.001% w/v, 0.005% w/v, 0.01% w/v, 0.05% w/v, 0.1% w/v, 0.25% w/v, 0.5% w/v, 0.75% w/v, 1.0% w/v, 1.25% w/v, 1.5% w/v, 1.75% w/v, 2.0% w/v, 2.25% w/v, 2.5% w/v, 2.75% w/v, 3.0% w/v, 3.25% w/v, 3.5% w/v 3.75% w/v, 4.0% w/v, 4.25% w/v, 4.5% w/v, 4.75% w/v, 5.0% w/v, or ranges between any of said topical anesthetic concentrations. The formulations may comprise combinations of anesthetics, in amounts that individually or in aggregate achieve(s) the stated anesthetic compositions.

In some embodiments, the topical, otic, ophthalmic, and nasal formulations described herein comprise a nonsteroidal antiinflammatory agent ("NSAID"). Suitable NSAIDs include ibuprofen, naproxen, diclofenac, celecoxib, etodolac, meloxicam, mefenamic acid, etoricoxib, ketorolac, salicylic acid, and indomethacin. In such embodiments, the formulations may comprise NSAID at a concentration of 0.001% w/v, 0.005% w/v, 0.01% w/v, 0.05% w/v, 0.1% w/v, 0.25% w/v, 0.5% w/v, 0.75% w/v, 1.0% w/v, 1.25% w/v, 1.5% w/v, 1.75% w/v, 2.0% w/v, 2.25% w/v, 2.5% w/v, 2.75% w/v, 3.0% w/v, 3.25% w/v, 3.5% w/v 3.75% w/v, 4.0% w/v, 4.25% w/v, 4.5% w/v, 4.75% w/v, 5.0% w/v, or ranges between any of said NSAID concentrations. The formulations may comprise combinations of NSAIDs, in amounts that individually or in aggregate achieve(s) the stated NSAID concentrations.

In some embodiments, the topical, otic, ophthalmic, and nasal formulations described herein may comprise an intraocular pressure ("IOP") reducing agent. Suitable TOP reducing agents include topical (3-adrenergic antagonists (e.g., timolol, betaxolol), carbonic anhydrase inhibitors (e.g., dorzolamide, brinzolamide), cholinergics (e.g., pilocarpine), α-adrenergic agonists (e.g., brimonidine), prostaglandins (e.g., latanoprost, travoprost, and unoprostone), and prostamides (e.g., bimatoprost). In such embodiments, the formulations may comprise TOP reducing agent at a concentration of 0.001% w/v, 0.005% w/v, 0.01% w/v, 0.05% w/v, 0.1% w/v, 0.25% w/v, 0.5% w/v, 0.75% w/v, 1.0% w/v, 1.25% w/v, 1.5% w/v, 1.75% w/v, 2.0% w/v, 2.25% w/v, 2.5% w/v, 2.75% w/v, 3.0% w/v, 3.25% w/v, 3.5% w/v 3.75% w/v, 4.0% w/v, 4.25% w/v, 4.5% w/v, 4.75% w/v, 5.0% w/v, or ranges between any of said TOP reducing agent concentrations. The formulations may comprise combinations of TOP reducing agents, in amounts that individually or in aggregate achieve(s) the stated TOP reducing agent concentrations.

In some embodiments, the topical, otic, ophthalmic, and nasal formulations described herein comprise an antioxidant. Suitable antioxidants include ascorbic acid, citric acid, betamercaptoethanol, cysteine, potassium metabisulfite, sodium metabisulfite, propyl gallate, butylated hydroxytoluene, butylated hydroxyanisole, sodium thiosulfate, and vitamin e. In such embodiments, the formulations may comprise antioxidant at a concentration of 0.001% w/v, 0.005% w/v, 0.01% w/v, 0.05% w/v, 0.1% w/v, 0.25% w/v, 0.5% w/v, 0.75% w/v, 1.0% w/v, 1.25% w/v, 1.5% w/v, 1.75% w/v, 2.0% w/v, 2.25% w/v, 2.5% w/v, 2.75% w/v, 3.0% w/v, 3.25% w/v, 3.5% w/v 3.75% w/v, 4.0% w/v, 4.25% w/v, 4.5% w/v, 4.75% w/v, 5.0% w/v, or ranges between any of said antioxidant concentrations. The formulations may comprise combinations of antioxidants, in amounts that individually or in aggregate achieve(s) the stated antioxidant concentrations.

In some embodiments, the topical, otic, ophthalmic, and nasal formulations described herein comprise a preservative. Suitable preservatives include benzalkonium chloride, benzyl alcohol, borates, parabens, cresols, benzoic acid, phenol, sorbic acid, benzethonium chloride. In such embodiments, the formulations may comprise preservative at a concentration of 0.001% w/v, 0.005% w/v, 0.01% w/v, 0.05% w/v, 0.1% w/v, 0.25% w/v, 0.5% w/v, 0.75% w/v, 1.0% w/v, 1.25% w/v, 1.5% w/v, 1.75% w/v, 2.0% w/v, 2.25% w/v, 2.5% w/v, 2.75% w/v, 3.0% w/v, 3.25% w/v, 3.5% w/v 3.75% w/v, 4.0% w/v, 4.25% w/v, 4.5% w/v, 4.75% w/v, 5.0% w/v, or ranges between any of said preservative concentrations. The formulations may comprise combinations of preservatives, in amounts that individually or in aggregate achieve(s) the stated preservative concentrations.

All ingredients of the topical, otic, ophthalmic, and nasal formulations described herein are pharmaceutical grade.

The disclosure also methods of treating an ophthalmic disorder in a patient in need of such treatment, comprising topically administering to ocular tissue of the patient a therapeutically effective amount of an ophthalmic corticosteroid formulation described herein. In such embodiments, the ophthalmic disorder can be a steroid-responsive inflammation of the ocular tissue.

In some embodiments, the therapeutically effective amount of the formulation is from 10 µl to 200 µl thereof. In some embodiments, the therapeutically effective amount of the formulation is about 20 µl, about 25 µl, about 30 µl, about 35 µl, about 40 µl, about 45 µl, about 50 µl, 55 µl, 60 µl, 65 µl, 70 µl, 75 µl, 80 µl, 85 µl, 90 µl, 95 µl, or 1000 µl of the formulation. In some embodiments, the ocular tissue is a cornea, a palpebral conjunctiva, a bulbar conjunctiva, and an anterior chamber, an eyelid, a sclera, a limbus, or a combination thereof. In some embodiments, the formulation is administered from once daily to eight times per day. In some embodiments, the formulation is administered one time per day, two times per day, three times per day, four times per day, five times per day, six times per day, seven times per day, and eight times per day, In some embodiments, the formulation is administered from one day to twenty-one consecutive days.

Example 1

Methods of Manufacturing and Formulation Ingredients. Topical otic, ophthalmic, and nasal aqueous suspensions described here were manufactured by initially making a polymeric stock solution of 1.2% w/v xanthan gum in about 95% w/v of purified water. The xanthan gum was dissolved in the purified water by mixing with either low-speed homogenization or overhead stirring, for a minimum of two hours at 25° C.±5° C. to ensure complete hydration of the polymer. This intermediate polymeric stock solution was then brought to the desired pH by adding Qs amount of NaOH or HCl, followed by the addition of Qs purified water. Corticosteroid excipient stock solutions were also prepared that comprised: 1.0% w/v, 1.4% w/v, or 2.0% w/v corticosteroid; 1.10% w/v sodium chloride; 0.20% w/v sodium sulfate; 0.01% w/v or 0.02% w/v tyloxapol; 0.02% w/v, 0.4% w/v, or 0.6% w/v disodium EDTA; 0.02% w/v benzalkonium chloride; 1.2% w/v propylene glycol; and about 95% w/v purified water. The corticosteroid excipient stock solution was then brought to the desired pH by adding a Qs amount of NaOH or HCl, followed by the addition of Qs purified water. The inactive excipients were dissolved in the purified water at 25° C.±5° C. by any one of a variety of suitable techniques that include homogenization, magnetic stirring, shaking, swirling, etc. The corticosteroid was dispersed in the excipient solution using the same technique used to solubilize the inactive excipients. The finished formulations were prepared by mixing equal volumes of the polymeric stock solution and the applicable corticosteroid excipient stock solution.

The Pred Forte control formulation was prepared by adding the prednisolone acetate and excipients listed in Table 1.2 to about 95% of the purified water. The inactive excipients were dissolved in the purified water at 25° C.±5° C. by any one of a variety of suitable techniques that include homogenization, magnetic stirring, shaking, swirling, etc. The corticosteroid was dispersed in the excipient solution using the same technique used to solubilize the inactive excipients. The Pred-Forte formulation was then brought to the desired pH by adding a Qs amount of NaOH or HCl, followed by the addition of Qs purified water.

Topical otic, ophthalmic, and nasal formulations having the ingredients set forth in Tables 1.1, 1.2, and 1.3 were manufactured according to the preceding method and studied in the redispersion assay set forth in Example 2.

TABLE 1.1

| Ingredient | C025-227-08 (A) Amount | C025-227-12 (A) Amount | C025-227-12 (B) Amount |
| --- | --- | --- | --- |
| Prednisolone Acetate | 0.50 w/v % | 0.50 w/v % | 1.00 w/v % |
| Xanthan gum | 0.60 w/v % | 0.60 w/v % | 0.60 w/v % |
| Sodium Chloride | 0.55 w/v % | 0.55 w/v % | 0.55 w/v % |
| Sodium Sulfate | 0.10 w/v % | 0.10 w/v % | 0.10 w/v % |
| Tyloxapol | 0.05 w/v % | 0.1 w/v % | 0.1 w/v % |
| Disodium EDTA | 0.01 w/v % | 0.01 w/v % | 0.01 w/v % |
| Benzalkonium Chloride | 0.01 w/v % | 0.01 w/v % | 0.01 w/v % |
| Propylene Glycol | 0.60 w/v % | 0.60 w/v % | 0.60 w/v % |
| HCl or NaOH | pH 5.7 | pH 5.7 | pH 5.7 |
| Purified water | 97.58 w/v % | 97.38 w/v % | 97.08 w/v % |

TABLE 1.2

| Ingredient | C025-227-14 (A) Amount | C025-227-14 (B) Amount | Pred-Forte Amount |
| --- | --- | --- | --- |
| Prednisolone Acetate | 0.50 w/v % | 1.00 w/v % | 1.00 w/v % |
| Xanthan gum | 0.60 w/v % | 0.60 w/v % | 0.0037 w/v % |
| Sodium Chloride | 0.55 w/v % | 0.55 w/v % | 1.075 w/v % |
| Sodium Sulfate | 0.10 w/v % | 0.10 w/v % | 0.011 w/v % |
| Tyloxapol | 0.05 w/v % | 0.05 w/v % | 0.505 w/v % |
| Disodium EDTA | 0.30 w/v % | 0.30 w/v % | 0.042 w/v % |
| Benzalkonium Chloride | 0.01 w/v % | 0.01 w/v % | 0.059 w/v % |
| Propylene Glycol | 0.60 w/v % | 0.60 w/v % | 0.305 w/v % |
| HCl or NaOH | pH 5.7 | pH 5.7 | 0.239 w/v % |
| Purified water | 97.29 w/v % | 96.79 w/v % | 96.76 w/v % |

TABLE 1.3

| Ingredient | C025-227-27(B) Amount | C025-227-27(C) Amount | C025-227-27(D) Amount | C025-227-27(E) Amount |
|---|---|---|---|---|
| Prednisolone Acetate | 0.50 w/v % | 0.70 w/v % | 0.50 w/v % | 0.70 w/v % |
| Xanthan gum | 0.60 w/v % | 0.60 w/v % | 0.60 w/v % | 0.60 w/v % |
| Sodium Chloride | 0.55 w/v % | 0.55 w/v % | 0.55 w/v % | 0.55 w/v % |
| Sodium Sulfate | 0.10 w/v % | 0.10 w/v % | 0.10 w/v % | 0.10 w/v % |
| Tyloxapol | 0.05 w/v % | 0.05 w/v % | 0.05 w/v % | 0.05 w/v % |
| Disodium EDTA | 0.20 w/v % | 0.20 w/v % | 0.30 w/v % | 0.30 w/v % |
| Benzalkonium Chloride | 0.01 w/v % | 0.01 w/v % | 0.01 w/v % | 0.01 w/v % |
| Propylene Glycol | 0.60 w/v % | 0.60 w/v % | 0.60 w/v % | 0.60 w/v % |
| TRIS Buffer | pH 7.4 | pH 7.4 | pH 7.4 | pH 7.4 |
| Purified water | 97.39 w/v % | 97.19 w/v % | 97.29 w/v % | 97.09 w/v % |

Example 2

Redispersion Assay. The redispersion properties of the topical otic, ophthalmic, and nasal corticosteroid formulations set forth in Example 1 were studied in the following redispersion assay. A 1.0 ml volume of each formulation was pelleted in a 1.5 ml vial, by centrifugation at 5000×G for two minutes. The pelleted material was subjected to consistent and vigorous wrist shaking. The shake-time required to fully resuspend the pelleted material is recorded. Formulations for which the pellet remained agglomerated and did not resuspend after 60 seconds or more of shaking are categorized as not redispersible ("NR"). The results of the redispersion assay are reported in Table 2. As can be seen formulations comprising 0.1% w/v EDTA were not redispersible, whereas formulations described herein that comprise greater than 0.1% w/v EDTA were redispersible in less than 60 seconds of wrist shaking.

TABLE 2

| Formulation | Redispersion time |
|---|---|
| Pred-Forte | NR |
| C025-227-08 (A) | NR |
| C025-227-12 (A) | NR |
| C025-227-12 (B) | NR |
| C025-227-14 (A) | 20 seconds |
| C025-227-14 (B) | 45 seconds |
| C025-227-27(B) | 20 seconds |
| C025-227-27(C) | 20 seconds |
| C025-227-27(D) | 20 seconds |
| C025-227-27(E) | 40 seconds |

Example 3

Viscosity Assay. The viscosity of topical otic, ophthalmic, and nasal aqueous suspension formulations investigated were determined using a Malvern Kinexus Rheometer. Each viscosity measurement tested a formulation sample size of 0.5 mL and ran a shear rate ramp to determine the viscosity flow curve of the sample at different shear rates. A software algorithm evaluated the resulting data, and a data point was taken when the shear rate reaches an equilibrium value. The viscosity flow curve test parameters set forth in Table 3.1 were applied to all formulations.

TABLE 3.1

| Viscosity Flow Curve Test Parameters | |
|---|---|
| Gap | 0.05 mm |
| Temperature | 25° C. |
| Start shear rate | 0.01 (1/sec) |
| End shear rate | 10,000 (1/sec) |
| Upper geometry | CP 1/100 |

Formulations manufactured according to the method described in Example 1 and having the ingredients set forth in Table 3.2, of which the xanthan gum was not deacetylated, were studied in the viscosity assay. The viscosity assay results are reported in Table 3.3.

TABLE 3.2

| Ingredient | C025-227-38 (A) Amount | C025-227-38 (B) Amount | C025-227-38 (C) Amount |
|---|---|---|---|
| Prednisolone Acetate | 0.70 w/v % | 0.70 w/v % | 0.70 w/v % |
| Xanthan gum | 0.60 w/v % | 0.60 w/v % | 0.0037 w/v % |
| Sodium Chloride | 0.55 w/v % | 0.55 w/v % | 1.075 w/v % |
| Sodium Sulfate | 0.10 w/v % | 0.10 w/v % | 0.011 w/v % |
| Tyloxapol | 0.05 w/v % | 0.05 w/v % | 0.505 w/v % |
| Disodium EDTA | 0.10 w/v % | 0.20 w/v % | 0.30 w/v % |
| Benzalkonium Chloride | 0.01 w/v % | 0.01 w/v % | 0.059 w/v % |
| Propylene Glycol | 0.60 w/v % | 0.60 w/v % | 0.305 w/v % |
| HCl or NaOH | pH 5.7 | pH 5.7 | 0.239 w/v % |
| Purified water | Qs to 100 w/v % | Qs to 100 w/v % | Qs to 100 w/v % |

TABLE 3.3

Stability of viscosity of topical otic, ophthalmic, nasal aqueous suspension formulations of corticosteroid prepared with non-deacetylated xanthan gum

| | Formulation No. | | |
|---|---|---|---|
| Analysis | C025-227-38 (A) Viscosity nCP | C025-227-38 (B) Viscosity nCP | C025-227-38 (C) Viscosity nCP |
| Initial | 6030.79 | 5796.11 | 5551.05 |
| 50° C, 1 week | 6564.27 | 6601.98 | 6508.55 |
| $\Delta_{(i-50° C., 1\ week)/i}*100$ | 8.85% | 13.90% | 17.25% |

Viscosity at shear rate 1 sec$^{-1}$ (cps)

It was surprisingly found that, despite containing xanthan gum that was not deacetylated, the C025-227-38 (A), (B), and (C) formulations demonstrated excellent viscosity stability properties.

Although the disclosure has been provided in the context of certain embodiments and examples, it will be understood by those skilled in the art that the disclosure extends beyond the specifically described embodiments to other alternative embodiments and/or uses and obvious modifications and equivalents thereof. Accordingly, the disclosure is not intended to be limited by the specific disclosures of embodiments and/or examples herein.

What is claimed is:

1. A pharmaceutical topical otic, ophthalmic, or nasal aqueous suspension formulation comprising:
   between 0.001% w/v and 5% w/v of a corticosteroid that is a cortisone, a prednisone, a prednisolone, a dexamethasone, a betamethasone, a mometasone, a triamcinolone, a fludrocortisone, a fluticasone, a deoxycorticosterone, an aldosterone, a beclomethasone, a loteprednol, or a combination thereof;
   between 0.3% w/v and 1.5% w/v of a xanthan gum;
   between 0.001% w/v and 2% w/v an ionic tonicity agent that is a calcium chloride, a magnesium chloride, a potassium chloride, a sodium chloride, a sodium sulfate, or a combination thereof;
   between 0.2% w/v and 2% w/v of a chelating agent that is an ethylenediaminetetraacetic acid ("EDTA"); and
   balance water,
   wherein the formulation has
   an osmolality of from 250 milliosmoles ("mOsm") to 350 mOsm;
   a viscosity of from 4000 centipoises ("cps") to 8000 cps;
   a pH from 5 to 6; and
   wherein the formulation is redispersible within 60 seconds.

2. The formulation of claim 1, further comprising between 0.001% w/v and 2% w/v of a nonionic surfactant that is a tyloxapol, a polysorbate 20, a polysorbate 60, a polysorbate 80, a polyethoxylated castor oil, or a combination thereof.

3. The formulation of claim 2, further comprising between 0.001% w/v and 2% w/v of a nonionic tonicity agent that is propylene glycol, glycerol, mannitol, sorbitol, xylitol, erythritol, lactitol, maltitol, isomalt, or a combination thereof.

4. The formulation of claim 3, wherein:
   the corticosteroid is the prednisolone;
   the ionic tonicity agent is the sodium chloride, the sodium sulfate, or a combination thereof;
   the nonionic surfactant is the tyloxapol; and
   the nonionic tonicity agent is the propylene glycol.

5. The formulation of claim 4, wherein the formulation comprises:
   between 0.25% w/v and 1.25% w/v of the prednisolone;
   between 0.2% w/v and 0.5% w/v of the EDTA;
   between 0.3% w/v and 1.0% w/v of the xanthan gum;
   between 0.25% w/w and 0.75% w/v of the sodium chloride;
   between 0.05% w/v and 0.15% w/v of the sodium sulfate;
   between 0.025% w/v and 0.25% w/v of the tyloxapol; and
   between 0.25% w/v and 0.75% w/v of the propylene glycol.

6. A pharmaceutical topical otic, ophthalmic, or nasal aqueous suspension formulation comprising:
   between 0.001% w/v and 5% w/v of a corticosteroid that is a cortisone, a prednisone, a prednisolone, a dexamethasone, a betamethasone, a mometasone, a triamcinolone, a fludrocortisone, a fluticasone, a deoxycorticosterone, an aldosterone, a beclomethasone, a loteprednol, or a combination thereof;
   between 0.3% w/v and 1.5% w/v of a non-deacetylated xanthan gum;
   between 0.001% w/v and 2% w/v of an ionic tonicity agent that is a calcium chloride, a magnesium chloride, a potassium chloride, a sodium chloride, a sodium sulfate, or a combination thereof;
   between 0.2% w/v and 2% w/v of a chelating agent that is an ethylenediaminetetraacetic acid ("EDTA"); and
   balance water,
   wherein the formulation has
   an osmolality of from 250 mOsm to 350 mOsm;
   a viscosity of 250 cps or more;
   a pH from 5 to 6; and
   wherein the formulation is 70% viscosity stable for one week at 50° C.

7. The formulation of claim 6, further comprising between 0.001% w/v and 2% w/v of a nonionic surfactant that is a tyloxapol, a polysorbate 20, a polysorbate 60, a polysorbate 80, a polyethoxylated castor oil, or a combination thereof.

8. The formulation of claim 7, further comprising between 0.001% w/v and 2% w/v of a nonionic tonicity agent that is propylene glycol, glycerol, mannitol, sorbitol, xylitol, erythritol, lactitol, maltitol, isomalt, or a combination thereof.

9. The formulation of claim 8, wherein:
   the corticosteroid is the prednisolone;
   the ionic tonicity agent is the sodium chloride, the sodium sulfate, or a combination thereof;
   the nonionic surfactant is the tyloxapol; and
   the nonionic tonicity agent is the propylene glycol.

10. The formulation of claim 9, wherein the formulation comprises:
    between 0.25% w/v and 1.25% w/v of the prednisolone;
    between 0.2% w/v and 0.5% w/v of the EDTA;
    between 0.3% w/v and 1.0% w/v of the non-deacetylated xanthan gum;
    between 0.25% w/w and 0.75% w/v of the sodium chloride;
    between 0.05% w/v and 0.15% w/v of the sodium sulfate;
    between 0.025% w/v and 0.25% w/v of the tyloxapol; and
    between 0.25% w/v and 0.75% w/v of the propylene glycol.

11. A method of treating an ophthalmic disorder in a patient in need thereof, said method comprising topically administering to ocular tissue of the patient a therapeutically effective amount of a formulation according to claim 1, wherein the ophthalmic disorder is steroid-responsive inflammation of the ocular tissue.

12. The method of claim 11, wherein the therapeutically effective amount of the formulation is from 10 µl to 200 µl thereof.

13. The method of claim 12, wherein the ocular tissue is a cornea, a palpebral conjunctiva, a bulbar conjunctiva, and an anterior chamber, an eyelid, a sclera, a limbus, or a combination thereof.

14. The method of claim 13, wherein the formulation is administered from once daily to eight times per day.

15. The method of claim 14, wherein the formulation is administered from one day to twenty-one consecutive days.

* * * * *